United States Patent
Kato et al.

(10) Patent No.: US 9,182,354 B2
(45) Date of Patent: Nov. 10, 2015

(54) ELECTROMAGNETIC WAVE MEASUREMENT DEVICE, MEASUREMENT METHOD, AND RECORDING MEDIUM

(75) Inventors: Eiji Kato, Miyagi (JP); Akiyoshi Irisawa, Miyagi (JP)

(73) Assignee: ADVANTEST CORPORATION, Tokyo (JP)

(*) Notice: Subject to any disclaimer, the term of this patent is extended or adjusted under 35 U.S.C. 154(b) by 635 days.

(21) Appl. No.: 13/458,274

(22) Filed: Apr. 27, 2012

(65) Prior Publication Data

US 2012/0286797 A1 Nov. 15, 2012

(30) Foreign Application Priority Data

May 12, 2011 (JP) ................................. 2011-106887

(51) Int. Cl.
 *G01N 21/35* (2014.01)
 *G01N 21/84* (2006.01)
 *G01N 21/3563* (2014.01)
 *G01N 21/3581* (2014.01)
 *G01N 21/95* (2006.01)

(52) U.S. Cl.
 CPC ........ *G01N 21/8422* (2013.01); *G01N 21/3563* (2013.01); *G01N 21/3581* (2013.01); *G01N 21/9508* (2013.01)

(58) Field of Classification Search
 None
 See application file for complete search history.

(56) References Cited

U.S. PATENT DOCUMENTS

| | | | |
|---|---|---|---|
| 7,697,122 B2 | 4/2010 | Yamashita et al. | |
| 8,183,528 B2 | 5/2012 | Kato et al. | |
| 2003/0149346 A1 | 8/2003 | Arnone et al. | |
| 2010/0108889 A1 | 5/2010 | Shen et al. | |
| 2010/0148070 A1 | 6/2010 | Ho | |
| 2010/0295534 A1 | 11/2010 | Nishina et al. | |
| 2011/0001048 A1 | 1/2011 | Nishina et al. | |
| 2012/0304756 A1 | 12/2012 | White et al. | |

FOREIGN PATENT DOCUMENTS

| | | |
|---|---|---|
| JP | 2003-525447 A | 8/2003 |
| JP | 2010/517031 | 5/2010 |
| WO | 2011/047016 | 4/2011 |

OTHER PUBLICATIONS

Felton, Linda A., "Characterization of Coating Systems", AAPS PharmSciTech, vol. 8 No. 4 (2007), pp. E1-E9.
Search report (partial) from E.P.O., mail date is Apr. 30, 2014.

(Continued)

*Primary Examiner* — Melissa Koval
*Assistant Examiner* — Stephen G Armstrong
(74) *Attorney, Agent, or Firm* — Greenblum & Bernstein, P.L.C.

(57) ABSTRACT

According to the present invention, an electromagnetic wave measurement device includes an electromagnetic wave output device, an electromagnetic wave detector and a measurement unit. The electromagnetic wave output device outputs an electromagnetic wave having a frequency equal to or more than 0.01 [THz] and equal to or less than 100 [THz] toward a device under test including at least two layers, and the electromagnetic wave detector detects reflected electromagnetic waves which are the electromagnetic waves reflected by the respective at least two layers. The measurement unit measures the device under test based on one or both of extreme values of electric fields of the respective reflected electromagnetic waves and a time difference between timings in which the electric fields of the respective reflected electromagnetic waves take the extreme values.

14 Claims, 4 Drawing Sheets

(56) References Cited

OTHER PUBLICATIONS

Office Action dated Dec. 21, 2012 by J.P.O. and English translation.
Yasui, T. et al., "Terahertz paintmeter for noncontact monitoring of thickness and drying progress in paint film". Applied Optics, vol. 44, Issue 32, Nov. 10, 2005, pp. 6849-6856.
Wilk R et al., "Highly Accurate THz Time-Domain Spectroscopy of Multilayer Structures", IEEE Journal of Selected Topics in Quantum Electronics, IEEE Service Center, Piscataway, NJ, US, vol. 14, No. 2, XP011206880, ISSN: 1077-260X, Mar. 1, 2008, pp. 392-398.
Yao-Chun Shen et al., "Development and Application of Terahertz Pulsed Imaging for Nondestructive Inspection of Pharmaceutical Tablet", IEEE Journal of Selected Topics in Quantum Electronics, IEEE Service Center, Piscataway, NJ, US, vol. 14, No. 2, XP011206874, ISSN: 1077-260X, Mar. 1, 2008, pp. 407-415.
Wataru Momose et al., "Applying terahertz technology for nondestructive detection of crack initiation in a film-coated layer on a swelling tablet", Results in Pharma Sciences, vol. 2, XP055114627, ISSN: 2211-2863, DOI: 10.1016/j.rinphs.2012.04.001, Apr. 13, 2012, pp. 29-37.
Search report from E.P.O. (Appl. No. 12167485.7), mail date is Aug. 26, 2014.

ELECTROMAGNETIC WAVE MEASUREMENT DEVICE, MEASUREMENT METHOD, AND RECORDING MEDIUM

TECHNICAL FIELD

The present invention relates to a measurement of a specimen having a layered structure without destroying the layers using an electromagnetic wave (the frequency of which is equal to or more than 0.01 [THz], and equal to or less than 100 [THz]) (such as a terahertz wave (the frequency of which is equal to or more than 0.03 [THz], and equal to or less than 10 [THz]), for example).

BACKGROUND ART

Among industrial products, there are many products having a layered structure to which coating is applied for a aesthetic reason, surface protection, or added functions. For example, a coating having a polymeric material as a main component for an added function such as appearance, bitterness masking, increased environmental resistance, and solubility control may be applied to a medical tablet.

According to a non-patent document 1, though quality evaluations for various tablet coating have been made, most of them are destructive tests and evaluations only focusing on the coating.

CITATION LIST (Patent Document 1) Japanese Unexamined Patent Application Publication No. 2010-517031
(Non-Patent Document 1) Linda A. Felton, "Characterization of Coating Systems," AAPS PharmSciTech, vol. 8, No. 4 (2007), pp. E1-E9

DISCLOSURE OF THE INVENTION

The present invention has an object to test a specimen having a layered structure by means of the nondestructive testing.

According to the present invention, an electromagnetic wave measurement device includes: an electromagnetic wave output device that outputs an electromagnetic wave having a frequency equal to or more than 0.01 [THz] and equal to or less than 100 [THz] toward a device under test including at least two layers; an electromagnetic wave detector that detects reflected electromagnetic waves which are the electromagnetic waves reflected by the respective at least two layers; and a measurement unit that measures the device under test based on one or both of extreme values of electric fields of the respective reflected electromagnetic waves and a time difference between timings in which the electric fields of the respective reflected electromagnetic waves take the extreme values.

According to the thus constructed electromagnetic wave measurement device, an electromagnetic wave output device outputs an electromagnetic wave having a frequency equal to or more than 0.01 [THz] and equal to or less than 100 [THz] toward a device under test including at least two layers. An electromagnetic wave detector detects reflected electromagnetic waves which are the electromagnetic waves reflected by the respective at least two layers. A measurement unit measures the device under test based on one or both of extreme values of electric fields of the respective reflected electromagnetic waves and a time difference between timings in which the electric fields of the respective reflected electromagnetic waves take the extreme values.

According to the electromagnetic wave measurement device of the present invention, the measurement unit may measure the device under test further based on an extreme value of an electric field of the electromagnetic wave output toward the device under test.

According to the electromagnetic wave measurement device of the present invention, the electromagnetic wave output device may output the electromagnetic wave to a metal surface; and the measurement unit may measure the extreme value of the electric field of the electromagnetic wave output toward the device under test as an extreme value of an electric field of an electromagnetic wave reflected from the metal surface.

According to the electromagnetic wave measurement device of the present invention, the measurement unit may measure the device under test based on ratios between the extreme values of the electric fields of the respective reflected electromagnetic waves, and the extreme value of the electric field of the electromagnetic wave output toward the device under test.

According to the electromagnetic wave measurement device of the present invention, the measurement unit may measure the device under test based on a product of the ratios between the extreme values of the electric fields of the respective reflected electromagnetic waves, and the extreme value of the electric field of the electromagnetic wave output toward the device under test, or an absolute value of the product.

According to the electromagnetic wave measurement device of the present invention, the measurement unit may measure the device under test based on a product of the product or the absolute value of the product and a thickness of one of the at least two layers.

According to the electromagnetic wave measurement device of the present invention, the measurement unit may measure the device under test based on a quotient of the product or the absolute value of the product divided by a thickness of one of the at least two layers.

According to the electromagnetic wave measurement device of the present invention, the device under test may be measured based on a ratio between the extreme values of the electric fields of the respective reflected electromagnetic waves.

According to the electromagnetic wave measurement device of the present invention, the measurement unit may measure a thickness of at least one of the at least two layers based on the time differences between the timings in which the electric fields of the respective reflected electromagnetic waves take the extreme values.

According to the electromagnetic wave measurement device of the present invention, the device under test may be measured based on a product of the ratios between the extreme values of the electric fields of the respective reflected electromagnetic waves or an absolute value of the product.

According to the electromagnetic wave measurement device of the present invention, the measurement unit may measure the device under test based on a product of the product or the absolute value of the product and a thickness of one of the at least two layers.

According to the electromagnetic wave measurement device of the present invention, the measurement unit may measure the device under test based on a quotient of the product or the absolute value of the product divided by a thickness of one of the at least two layers.

According to the electromagnetic wave measurement device of the present invention, the measurement unit may measure the device under test based on a product of the extreme values of the electric fields of the respective reflected electromagnetic waves or an absolute value of the product.

According to the present invention, an electromagnetic wave measurement method includes: an electromagnetic wave output step that outputs an electromagnetic wave having a frequency equal to or more than 0.01 [THz] and equal to or less than 100 [THz] toward a device under test including at least two layers; an electromagnetic wave detecting step that detects reflected electromagnetic waves which are the electromagnetic waves reflected by the respective at least two layers; and a measurement step that measures the device under test based on one or both of extreme values of electric fields of the respective reflected electromagnetic waves and a time difference between timings in which the electric fields of the respective reflected electromagnetic waves take the extreme values.

The present invention is a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test including at least two layers; and an electromagnetic wave detector that detects reflected electromagnetic waves which are the electromagnetic waves reflected by the respective at least two layers; the electromagnetic wave measurement process including: a measurement step that measures the device under test based on one or both of extreme values of electric fields of the respective reflected electromagnetic waves and a time difference between timings in which the electric fields of the respective reflected electromagnetic waves take the extreme values.

The present invention is a computer-readable medium having a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test including at least two layers; and an electromagnetic wave detector that detects reflected electromagnetic waves which are the electromagnetic waves reflected by the respective at least two layers; the electromagnetic wave measurement process including: a measurement step that measures the device under test based on one or both of extreme values of electric fields of the respective reflected electromagnetic waves and a time difference between timings in which the electric fields of the respective reflected electromagnetic waves take the extreme values.

BEST MODE FOR CARRYING OUT THE INVENTION

A description will now be given of an embodiment of the present invention referring to drawings.

Figure 1:
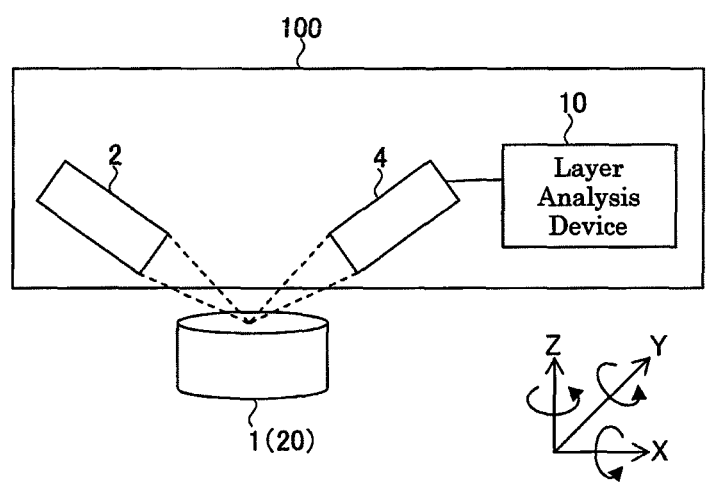
FIG. 1 is a diagram showing a configuration of an electromagnetic wave measurement device 100 according to the embodiment of the present invention.
Figure 2:
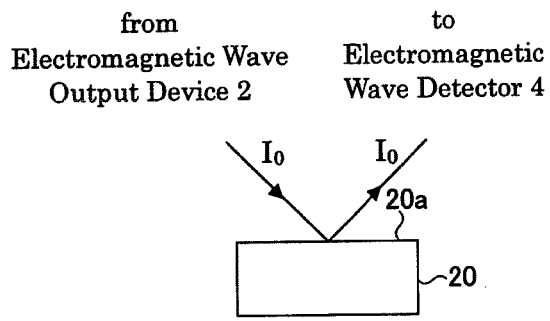
FIG. 2 is a diagram showing an electromagnetic wave reflected by a reference mirror 20 (refer to FIG. 2(a)), a measurement result thereof (refer to FIG. 2(b)), electromagnetic waves reflected by a device under test (DUT) 1 having a two-layered structure (refer to FIG. 2(c)), and a measurement result thereof (refer to FIG. 2(d))
Figure 2:
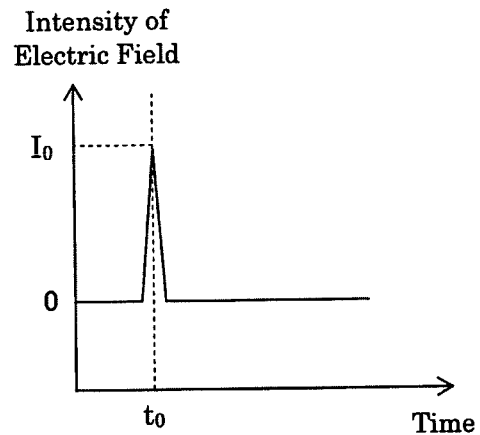
Figure 2:
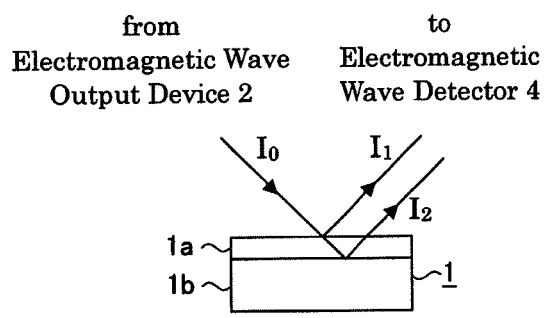
Figure 2:
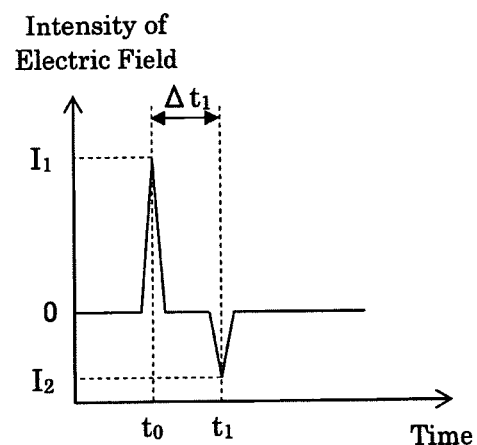

FIG. 1 is a diagram showing a configuration of an electromagnetic wave measurement device 100 according to the embodiment of the present invention. FIG. 2 is a diagram showing an electromagnetic wave reflected by a reference mirror 20 (refer to FIG. 2(a)), a measurement result thereof (refer to FIG. 2(b)), electromagnetic waves reflected by a device under test (DUT) 1 having a two-layered structure (refer to FIG. 2(c)), and a measurement result thereof (refer to FIG. 2(d)).

The electromagnetic wave measurement device 100 according to the embodiment of the present invention includes an electromagnetic wave output device 2, an electromagnetic wave detector 4 and a layer analysis device (measurement unit) 10. The electromagnetic wave measurement device 100 is used for measuring the DUT 1.

Figure 4:
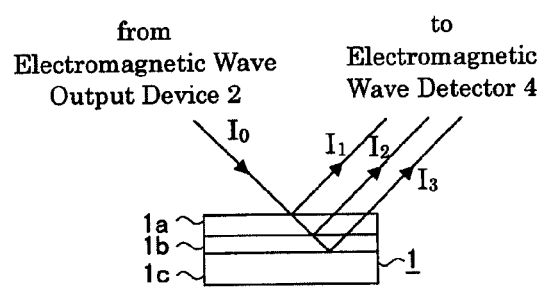
FIG. 4 is a diagram showing electromagnetic waves reflected by the DUT 1 having a three-layered structure (refer to FIG. 4(a)), and a measurement result thereof (refer to FIG. 4(b)).
Figure 4:
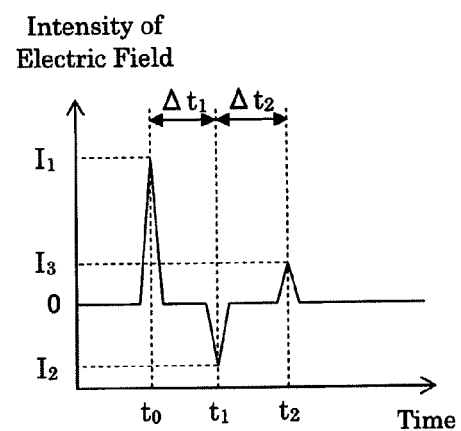

The DUT 1 includes a layer 1a and a layer 1b referring to FIG. 2(c). The layer 1a is above the layer 1b. Though the DUT 1 has two layers according to the embodiment of the present invention, the DUT 1 may have two or more layers. FIG. 4 is a diagram showing electromagnetic waves reflected by the DUT 1 having a three-layered structure (refer to FIG. 4(a)), and a measurement result thereof (refer to FIG. 4(b)). The DUT 1 may include a layer 1a, a layer 1b, and a layer 1c referring to FIG. 4(a). The layer 1a is above the layer 1b, and the layer 1b is above the layer 1c.

The electromagnetic wave output device 2 outputs an electromagnetic wave having a frequency equal to or more than 0.01 [THz] and equal to or less than 100 [THz] toward the DUT 1. The frequency of the electromagnetic wave output toward the DUT 1 includes a terahertz wave band (such as equal to or more than 0.03 [THz] and equal to or less than 10 [THz]). According to the embodiment of the present invention, it is assumed to employ a terahertz wave as an example of the electromagnetic wave.

It should be noted that the electromagnetic wave output device 2 may output the terahertz wave toward a reference mirror 20 before irradiating the terahertz wave toward the DUT 1 (refer to FIG. 2(a)). The reference mirror 20 includes a metal surface 20a (material is gold, silver, or aluminum, for example), and the reflectance of the metal surface 20a is approximately 100%.

The terahertz wave output toward the DUT 1 is reflected respectively by the layers (layer 1a, layer 1b, and layer 1c) of the DUT 1. The electromagnetic wave detector 4 detects reflected electromagnetic waves which are electromagnetic waves (such as terahertz waves) reflected respectively by the layers of the DUT 1.

The DUT 1 may be scanned along the x axis, the y axis, and the z axis, and may then be scanned while the DUT 1 is rotated about the x axis, the y axis, and the z axis. Moreover, the electromagnetic wave output device 2 and the electromagnetic wave detector 4 may be scanned along the x axis, the y axis, and the z axis, and may then be scanned while the electromagnetic wave output device 2 and the electromagnetic wave detector 4 are rotated about the x axis, the y axis, and the z axis.

The layer analysis device (measurement unit) 10 measures the DUT 1 based on either on or both of extreme values ($I_1$, $I_2$, and $I_3$) of electric fields of the reflected electromagnetic waves, and time differences $\Delta t_1$ and $\Delta t_2$ between timings ($t_0$, $t_1$, and $t_2$) in which the electric fields of the respective reflected electromagnetic waves take the extreme values.

Figure 3:
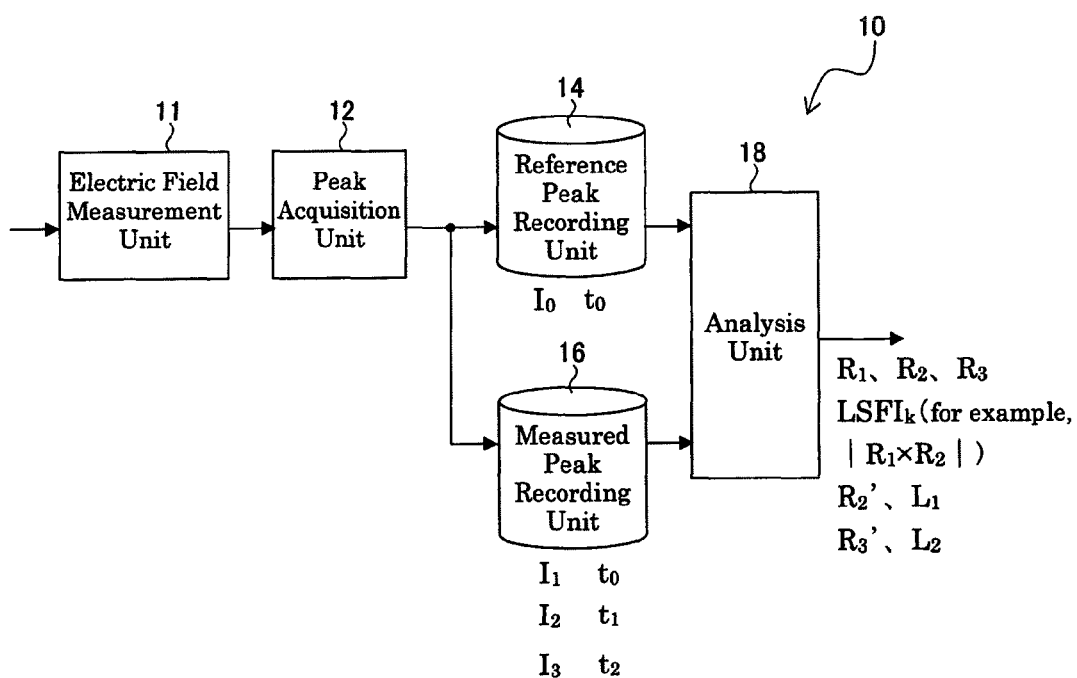
FIG. 3 is a functional block diagram showing a configuration of the layer analysis device (measurement unit) 10.

FIG. 3 is a functional block diagram showing a configuration of the layer analysis device (measurement unit) 10. The layer analysis device 10 includes an electric field measurement unit 11, a peak acquisition unit 12, a reference peak recording unit 14, a measured peak recording unit 16, and an analysis unit 18.

The electric field measurement unit 11 measures an intensity of the electric field as a function of time from the detection result by the electromagnetic wave detector 4. The intensity of the electric field is shown in FIG. 2(*b*) (case in which the terahertz wave is reflected by the reference mirror 20) and FIG. 2(*d*) (case in which the terahertz wave is reflected by the respective layers of the DUT 1). The electric field measurement unit 11 may carry out signal processing such as deconvolution.

The peak acquisition unit 12 acquires an extreme value in an intensity of an electric field measured by the electric field measurement unit 11 and a timing thereof. For example, the peak acquisition unit 12 acquires an extreme value $I_0$ of an electric field of the terahertz wave reflected from the metal surface 20*a* while the extreme value $I_0$ is associated with a time $t_0$ referring to FIG. 2(*b*). For example, the peak acquisition unit 12 acquires an extreme value $I_1$ of an electric field of the reflected electromagnetic wave, which is the terahertz wave reflected by the layer 1*a*, while the extreme value $I_1$ is associated with a time $t_0$, and further acquires an extreme value $I_2$ of an electric field of the reflected electromagnetic wave, which is the terahertz wave reflected by the layer 1*b*, while the extreme value $I_2$ is associated with a time $t_1$ referring to FIG. 2(*d*).

If the DUT 1 has the three-layered structure (refer to FIG. 4(*a*)), the peak acquisition unit 12 further acquires an extreme value $I_3$ of an electric field of the reflected electromagnetic wave which is the terahertz wave reflected by the layer 1*c* while the extreme value $I_3$ is associated with a time $t_2$ (refer to FIG. 4(*b*)). Moreover, it is conceivable that the DUT 1 has four or more layers 1*k* (k is an integer from 1 to 4 or more, and a layer denoted by k becomes farther from the electromagnetic wave output device 2 as k increases). In this case, the peak acquisition unit 12 acquires an extreme value $I_k$ of an electric field of a reflected electromagnetic wave, which is the terahertz wave reflected by the layer 1*k*, while the extreme value $I_k$ is associated with a time $t_{k-1}$. It should be noted that the layer 1*a* corresponds to a layer 1$_1$, the layer 1*b* corresponds to a layer 1$_2$, and the layer 1*c* corresponds to a layer 1$_3$.

The reference peak recording unit 14 records the extreme value of the intensity of the electric field of the terahertz wave reflected from the metal surface 20*a* and the timing thereof out of the acquisition result by the peak acquisition unit 12. For example, the reference peak recording unit 14 records the extreme value $I_0$ while the extreme value $I_0$ is associated with the time $t_0$. Though the recorded content of the reference peak recording unit 14 is the extreme value of the electric field of the electromagnetic wave reflected from the metal surface 20*a*, this extreme value can be considered as an extreme value of an electric field of the electromagnetic wave output toward the DUT 1.

The measured peak recording unit 16 records the extreme values of the intensity of the electric fields of the terahertz waves reflected from the respective layers (layers 1*a*, 1*b*, and 1*c*) of the DUT 1 and the timings thereof out of the acquisition result by the peak acquisition unit 12. For example, the measured peak recording unit 16 records the extreme value $I_1$ while the extreme value $I_1$ is associated with the time to, and the extreme value $I_2$ while the extreme value $I_2$ is associated with the time $t_1$. Further, for example, the measured peak recording unit 16 records the extreme value $I_3$ while the extreme value $I_3$ is associated with the time $t_2$. As a more general representation, an extreme value $I_k$ is recorded while the extreme value $I_k$ is associated with the time $t_{k-1}$.

The analysis unit 18 analyzes the layers 1*a*, 1*b*, and 1*c* of the DUT 1 based on the recorded content of the reference peak recording unit 14 (the extreme value of the electric field of the electromagnetic wave output toward the DUT 1) and the recorded content of the measured peak recording unit 16.

The analysis unit 18 reads the extreme values $I_1$ and $I_2$ of the electric fields of the respective reflected electromagnetic waves from the measured peak recording unit 16, and reads the extreme value $I_0$ of the electric field of the electromagnetic wave output toward the DUT 1 from the reference peak recording unit 14. The analysis unit 18 acquires a reflectance $R_1=I_1/I_0$ and a reflectance $R_2=I_2/I_0$, which are ratios between the extreme values $I_1$ and $I_2$ of the electric fields of the respective reflected electromagnetic waves and the extreme value $I_0$ of the electric field of the electromagnetic wave output toward the DUT 1. They are respectively reflectances of the layers 1*a* and 1*b* of the DUT 1.

If a terahertz wave pulse is made incident to an incident surface of the DUT as p-polarized light, the reflectance $R_1$ is represented as $(n_1 \cos \alpha - n_0 \cos \beta)/(n_1 \cos \alpha + n_0 \cos \beta)$ according to the Fresnel's formula. It should be noted that $n_0$ denotes a refractive index of air which is a medium in which the DUT 1 is disposed, $n_1$ denotes a refractive index of the layer 1*a*, a denotes an incident angle of the terahertz wave to the DUT 1, and β denotes a refraction angle of the terahertz wave which has transmitted through the layer 1*a*.

On this occasion, $n_0$ is constant, and therefore the reflectance $R_1$ changes depending on the refractive index $n_1$ of the layer 1*a*. Further, the refractive index of a material can be considered as a value indicating the density of the material. Thus, the acquisition of the reflectance $R_1$ leads to the measurement of the density of the layer 1*a* of the DUT 1.

More generally, a reflectance $R_k$ of the layer 1*k* is represented by $(n_k \cos \beta_{k-1} - n_{k-1} \cos \beta_k)/(n_k \cos \beta_{k-1} + n_{k-1} \cos \beta_k)$ where a refraction angle of the layer 1*k* is $\beta_k$, and an incident angle to the layer 1*k* (namely refraction angle of the layer 1$_{k-1}$) is $\beta_{k-1}$.

The reflectance $R_1$ is $I_1/I_0$, and is represented as $R_1=(n_1 \cos \alpha - n_0 \cos \beta)/(n_1 \cos \alpha + n_0 \cos \beta)$ according to the Fresnel's formula. Moreover, a relationship $\sin \alpha/\sin \beta = n_1/n_0$ holds true according to the Snell's law. The reflectance $R_1$ is acquired from the measurement result, and the incident angle α and the refractive index no of the air are known. Thus, the refraction angle β and the refractive index $n_1$ of the layer 1*a* can be acquired according to the above-mentioned equations.

Then, the reflectance $R_2$ of the layer 1*b* (layer 1$_2$) is represented as $(n_2 \cos \beta - n_1 \cos \beta_2)/(n_2 \cos \beta + n_1 \cos \beta_2)$ where the refraction angle of the layer 1*b* is $\beta_2$, and the incident angle to the layer 1*b* (namely, refraction angle of the layer 1*a*) is β. Moreover, a relationship $\sin \beta/\sin \beta_2 = n_2/n_1$ holds true according to the Snell's law. The reflectance $R_2$ is acquired from the measurement result, and the incident angle β and the refractive index $n_1$ are known. Thus, the refraction angle $\beta_2$ and the refractive index $n_2$ of the layer 1*b* can be acquired according to the above-mentioned equations.

Then, the refraction angle $\beta_k$ and the refractive index $n_k$ of the layer 1*k* can be acquired in a similar manner.

If the terahertz wave pulse is made incident to the DUT 1 vertically ($\alpha=\beta=0$ holds true), and $n_0=1$, the refractive index $n_1$ of the layer 1a is acquired by solving the reflectance $R_1 = (n_1 \cos\alpha - n_0 \cos)/(n_1 \cos\alpha + n_0 \cos\beta) = (n_1-1)/(n_1+1)$ in terms of $n_1$. In other words, $n_1=(1+R_1)/(1-R_1)$ is acquired.

The reflectance $R_2$ changes according to a difference between the refractive index $n_1$ of the layer 1a and the refractive index $n_2$ of the layer 1b (corresponding to a difference in density between the layers 1a and 1b) according to the Fresnel's formula. Moreover, the reflectance $R_2$ is determined by a relationship in magnitude between $n_1$ and $n_2$.

$R_2>0$ ($n_1<n_2$)
$R_2<0$ ($n_1>n_2$)
hold true.

The reflectance $R_2$ represents the relationship in magnitude of the refractive index between the layers 1a and 1b, and clearness of a boundary surface between the layers 1a and 1b of the DUT 1. Thus, the acquisition of the reflectance $R_2$ leads to the measurement of the layers 1a and 1b of the DUT 1. Moreover, based on the reflectance $R_2$, it is possible to nondestructively analyze characteristics such as detachability of the boundary surface between the layers 1a and 1b and flexibility in response to expansion of the boundary surface.

It should be noted that the reflectance of the layer 1k, $R_k=I_k/I_0$ can be acquired in a similar manner. Moreover, based on the reflectance $R_k$, it is possible to analyze nondestructively characteristics such as detachability of the boundary surface between the layers $\mathbf{1}_{k-1}$ and 1k and flexibility in response to expansion of the boundary surface.

Moreover, the analysis unit 18 acquires a ratio $R_2'=I_2/I_1$ between the extreme values $I_1$ and $I_2$ of the electric fields of the respective reflected electromagnetic waves. The ratio $R_2'$, as the reflectance $R_2$, represents a relationship in magnitude of the refractive index between the layers 1a and 1b, and clearness of the boundary surface between the layers 1a and 1b of the DUT 1. The ratio $R_2'$ is the extreme value $I_2$ normalized by $I_1$, which is an index indicating the density of the layer 1a, and it is thus possible to make evaluation restraining absorption of the terahertz wave pulse, which is reflected from the boundary surface between the layers 1a and 1b, upon passing through the layer 1a and the like. Thus, the acquisition of the ratio $R_2'$ leads to the measurement of the layers 1a and 1b of the DUT 1. In other words, the acquisition of the ratio $R_2'$, as the acquisition of $R_2$, enables an analysis of characteristics such as detachability of the boundary surface and flexibility in response to expansion of the boundary surface.

The analysis unit 18 acquires a ratio $R_k'=I_k/I_{k-1}$ between the extreme values $I_k$ and $I_{k-1}$ of the electric fields of the respective reflected electromagnetic waves. As a result, the layer 1k can be analyzed restraining influence from the layer 1a to the layer $\mathbf{1}_{k-1}$.

Further, the analysis unit 18 measures one or more of two or more layers based on a time difference $\Delta t_1 = t_1 - t_0$ between the timings $t_0$ and $t_1$ at which the electric fields of the respective reflected electromagnetic waves take the extreme values $I_1$ and $I_2$. For example, the analysis unit 18 can acquire a thickness $L_1$ of the layer 1a of the DUT 1 as $c\,\Delta t_1/(2n_1)$. It should be noted that c denotes the light speed, and it is assumed that the terahertz wave is made incident to the DUT 1 vertically. It should be noted that the analysis unit 18 can acquire a thickness $L_2$ of the layer 1b of the DUT 1 as $c\,\Delta t_2/(2n_2)$ based on $\Delta t_2 = t_2 - t_1$. It should be noted that $n_2$ can be acquired as described above. Moreover, the analysis unit 18 can acquire a thickness $L_k$ of the layer 1k of the DUT 1 as $c\,\Delta t_k/(2n_k)$ according to $\Delta t_k = t_k - t_{k-1}$. It should be noted that $n_k$ can be acquired as described above.

Moreover, the analysis unit 18 acquires an index (Layer Strength and Flexibility Index: LSFI) relating to strength and flexibility of an industrial product having a layered structure or a coating. It should be noted that LSFI is an index newly proposed by the present applicant. Moreover, $LSFI_1$ is an index for the layer 1a and $LSFI_k$ is an index for the layer 1k.

For example, the analysis unit 18 acquires a product $R_1 \times R_2$ of the reflectance $R_1$ and the reflectance $R_2 = I_2/I_0$ as $LSFI_1$, and then acquires an absolute value thereof $|R_1 \times R_2|$. As $LSFI_1 = |R_1 \times R_2|$ increases, it can be estimated that the strength and the flexibility of the layer 1a increase. Thus, the analysis unit 18 measures the layer 1a of the DUT 1 based on the product $R_1 \times R_2$ of the reflectance $R_1$ and the reflectance $R_2$. It should be noted that, more generally, the analysis unit 18 acquires a product $R_k \times R_{k+1}$ of the reflectance $R_k$ and the reflectance $R_{k+1}$ as $LSFI_k$, and then acquires an absolute value thereof $|R_k \times R_{k+1}|$. As $LSFI_k = |R_k \times R_{k+1}|$ increases, it can be estimated that the strength and the flexibility of the layer 1k increase.

It should be noted that the reflectance $R_k = I_k/I_0$ of the layer 1k is a ratio between the extreme value $I_k$ of the electric field of the reflected electromagnetic wave and the extreme value $I_0$ of the electric field of the electromagnetic wave output toward the DUT 1.

Moreover, the analysis unit 18 acquires the product $R_1 \times R_2$ of the reflectance $R_1$ and the reflectance $R_2 = I_2/I_0$ as $LSFI_1$. It is possible to analyze a relationship in difference in density between the neighboring layers 1a and 1b according to whether $LSFI_1 = R_1 \times R_2$ is positive or negative. Thus, the analysis unit 18 measures the layers 1a and 1b of the DUT 1 based on the product $R_1 \times R_2$ of the reflectance $R_1$ and the reflectance $R_2$. It should be noted that, more generally, the analysis unit 18 acquires a product $R_k \times R_{k+1}$ of the reflectance $R_k$ and the reflectance $R_{k+1}$ as $LSFI_k$. It is possible to analyze a relationship in difference in density between the neighboring layers 1k and $\mathbf{1}_{k+1}$ according to whether $LSFI_k = R_k \times R_{k+1}$ is positive or negative.

Further, the analysis unit 18 acquires a product of the extreme values $I_1$ and $I_2$, or an absolute value thereof as $LSFI_1$. As $LSFI_1$ increases, it can be estimated that the strength and the flexibility of the layer 1a increase. If the product of the extreme values $I_1$ and $I_2$ is acquired as $LSFI_1$, it is possible to analyze a relationship in difference in density between the neighboring layers 1a and 1b. More generally, the analysis unit 18 acquires a product of the extreme values $I_k$ and $I_{k+1}$, or an absolute value thereof as $LSFI_k$. As $LSFI_k$ increases, it can be estimated that the strength and the flexibility of the layer 1k increase. If the product of the extreme values $I_k$ and $I_{k+1}$ is acquired as $LSFI_k$, it is possible to analyze a relationship in difference in density between the neighboring layers 1k and $\mathbf{1}_{k+1}$.

Moreover, the analysis unit 18 acquires $R_k' \times R_{k+1}/L_k$ or an absolute value thereof as $LSFI_k$. If there is a correlation between the density and the thickness of a layer, it is possible to make analysis while the influence of the layer thickness is normalized. Further, the analysis unit 18 acquires $R_k \times R_{k+1} \times L_k$ or an absolute value thereof as $LSFI_k$. An analysis enhancing the influence of the layer thickness can be provided.

Further, the analysis unit 18 acquires $R_k' \times R_{k+1}'$ or an absolute value thereof as $LSFI_k$. If the DUT 1 is multi-layered, and absorptions of the respective layers are not negligible, an analysis relating to the strength and the flexibility of a layer farther than the layer 1a from the electromagnetic wave output device 2 can be carried out nondestructively.

It should be noted that the ratio $R_k' = I_k/I_{k-1}$ is a ratio between the extreme values $I_k$ and $I_{k-1}$ of the electric fields of the reflected electromagnetic waves.

Moreover, the analysis unit 18 acquires $R_k' \times R_{k+1}'/L_k$ or an absolute value thereof as $LSFI_k$. If there is a correlation between the density and the thickness of a layer, it is possible to make analysis while the influence of the layer thickness is normalized. Further, the analysis unit 18 acquires $R_k' \times R_{k+1}' \times L_k$ or an absolute value thereof as $LSFI_k$. An analysis enhancing the influence of the layer thickness can be provided.

A description will now be given of an operation of the embodiment of the present invention.

First, the electromagnetic wave output device 2 outputs the terahertz wave toward the reference mirror 20. Then, approximately 100% of the terahertz wave is reflected, and is detected by the electromagnetic wave detector 4. The detection result is fed to the layer analysis device (measurement unit) 10, and the extreme values $I_0$ and the time $t_0$ of the electric field of the terahertz wave are acquired by the electric field measurement unit 11 and the peak acquisition unit 12 (refer to FIG. 2(a) and FIG. 2(b)), and are recorded in the reference peak recording unit 14.

Then, the electromagnetic wave output device 2 outputs the terahertz wave toward the DUT 1. On this occasion, the DUT 1, or the electromagnetic wave output device 2 and the electromagnetic wave detector 4 are scanned. Then, the terahertz wave is reflected by the layers 1a and 1b, and is detected by the electromagnetic wave detector 4. The detection result is fed to the layer analysis device (measurement unit) 10, and the extreme values $I_1$ and the time $t_0$, and the extreme value $I_2$ and the time $t_1$ of the electric field of the terahertz wave are acquired by the electric field measurement unit 11 and the peak acquisition unit 12 (refer to FIGS. 2(c) and 2(d)), and are recorded in the measured peak recording unit 16. Further, the extreme value $I_3$ and the time $t_2$ are acquired (refer to FIGS. 4(a) and 4(b)), and are recorded in the measured peak recording unit 16.

The analysis unit 18 analyzes the layers 1a, 1b, and 1c of the DUT 1 based on the recorded content of the reference peak recording unit 14 and the recorded content of the measured peak recording unit 16.

For example, the analysis unit 18 acquires the reflectance $R_1 = I_1/I_0$, the reflectance $R_2 = I_2/I_0$, the reflectance $R_3 = I_3/I_0$, $LSFI_k$ ($|R_1 \times R_2|$, for example), the ratio $R_2' = I_2/I_1$, the ratio $R_3' = I_3/I_2$, the thickness of the layer 1a, $L_1 = c \, \Delta t_1/(2n_1)$, and the thickness of the layer 1b, $L_2 = c \, \Delta t_2/(2n_2)$.

According to the embodiment of the present invention, a specimen having a layered structure can be tested by means of the nondestructive test.

Moreover, according to the embodiment of the present invention, a layered specimen having layers from several microns to several centimeters can be analyzed using the terahertz wave.

The reflectances $R_1$ and $R_2$, and the thickness of the layer 1a are acquired by the analysis unit 18, and can be used to nondestructively acquire, as indices, the strength, detachability, and flexibility of an industrial product having a layered structure or an applied coating. As an example of such an industrial product, there is a film-coated tablet which is a medicine, and is generally constructed by a first layer, which is a film coat layer, and a second layer (inner layer), which is an uncoated tablet constructed by a principal agent, an excipient, and an additive.

The film coat layer may present a detachment and a crack due to a storage environment and the like, resulting in a problem in terms of quality. The refractive index (density) of the film coat layer and a difference in refractive index (density) of a boundary surface between the film coat layer and the uncoated tablet are not determined only by a chemical composition of a film coat base, but a scale and operation conditions of a film coating device.

It is necessary to select an optimum film coat base, and to optimize coating process conditions for satisfying specifications and a quality as a product of the film-coated tablet, and they have been optimized only by empirical methods.

However, the analysis of a film coat tablet according to the present invention enables quantitatively obtaining indices of the density of the film coat layer and a state of the boundary surface between the film coat layer and the uncoated tablet.

For example, as the density of the film coat layer of the film-coated tablet increases, the strength thereof increases. Moreover, as the difference in density at the boundary surface between the film coat layer and the uncoated tablet increases, the boundary surface becomes clearer, and the detachability increases. From another point of view, it is considered that resistance to the expansion (flexibility) increases.

Moreover, the above-described embodiments may be realized in the following manner. A computer is provided with a CPU, a hard disk, and a media (such as a floppy disk (registered trade mark) and a CD-ROM) reader, and the media reader is caused to read a medium recording a program realizing the above-described respective components such as the layer analysis device (measurement unit) 10, thereby installing the program on the hard disk. This method may also realize the above-described functions.

The invention claimed is:

1. An electromagnetic wave measurement device comprising:
   an electromagnetic wave output device that outputs an electromagnetic wave having a frequency equal to or more than 0.01 THz and equal to or less than 100 THz toward a device under test including at least two layers;
   an electromagnetic wave detector that detects reflected electromagnetic waves which are electromagnetic waves reflected by the respective at least two layers; and
   a measurer that measures the device under test based on at least two extreme values of electric fields of the respective reflected electromagnetic waves and a time difference between times at which the electric fields of the respective reflected electromagnetic waves take the at least two extreme values, the at least two extreme values including a first extreme value and a second extreme value,
   wherein the measurer measures the device under test based on a product of a first ratio and a second ratio, or an absolute value of the product, the first ratio being a ratio of the first extreme value to an extreme value of an electric field of the electromagnetic wave output toward the device under test, the second ratio being a ratio of the second extreme value to the extreme value of the electric field of the electromagnetic wave output toward the device under test.

2. The electromagnetic wave measurement device according to claim 1, wherein:
   the electromagnetic wave output device outputs the electromagnetic wave towards a metal surface; and
   the measurer measures the extreme value of the electric field of the electromagnetic wave output toward the device under test as an extreme value of an electric field of an electromagnetic wave reflected from the metal surface.

3. The electromagnetic wave measurement device according to claim 2, wherein the measurer measures the device under test based on a product of the product or the absolute value of the product and a thickness of one of the at least two layers.

4. The electromagnetic wave measurement device according to claim 2, wherein the measurer measures the device under test based on a quotient of the product or the absolute value of the product divided by a thickness of one of the at least two layers.

5. The electromagnetic wave measurement device according to claim 1, wherein the measurer measures the device under test based on a product of the product or the absolute value of the product and a thickness of one of the at least two layers.

6. The electromagnetic wave measurement device according to claim 1, wherein the measurer measures the device under test based on a quotient of the product or the absolute value of the product divided by a thickness of one of the at least two layers.

7. The electromagnetic wave measurement device according to claim 1, wherein the device under test is measured based on a ratio between the at least two extreme values of the electric fields of the respective reflected electromagnetic waves.

8. The electromagnetic wave measurement device according to claim 1, wherein the measurer measures a thickness of at least one of the at least two layers based on the time differences between the times at which the electric fields of the respective reflected electromagnetic waves take the at least two extreme values.

9. The electromagnetic wave measurement device according to claim 1, wherein the at least two extreme values further includes a third extreme value
the device under test is measured based on a product of a third ratio and a fourth ratio, or an absolute value of the product of the third ratio and the fourth ratio, the third ratio being a ratio of the first extreme value to the second extreme value, the fourth ratio being a ratio of the second extreme value to the third extreme value.

10. The electromagnetic wave measurement device according to claim 9, wherein the measurer measures the device under test based on a product of the product of the third ratio and the fourth ratio or the absolute value of the product of the third ratio and the fourth ratio and a thickness of one of the at least two layers.

11. The electromagnetic wave measurement device according to claim 9, wherein the measurer measures the device under test based on a quotient of the product of the third ratio and the fourth ratio or the absolute value of the product of the third ratio and the fourth ratio divided by a thickness of one of the at least two layers.

12. The electromagnetic wave measurement device according to claim 1, wherein the measurer measures the device under test based on a product of the at least two extreme values of the electric fields of the respective reflected electromagnetic waves or an absolute value of the product.

13. An electromagnetic wave measurement method comprising:
outputting an electromagnetic wave having a frequency equal to or more than 0.01 THz and equal to or less than 100 THz toward a device under test including at least two layers;
detecting reflected electromagnetic waves which are electromagnetic waves reflected by the respective at least two layers; and
measuring the device under test based on at least two extreme values of electric fields of the respective reflected electromagnetic waves and a time difference between times at which the electric fields of the respective reflected electromagnetic waves take the at least two extreme values, the at least two extreme values including a first extreme value and a second extreme value,
wherein the device under test is measured based on a product of a first ratio and a second ratio, or an absolute value of the product, the first ratio being a ratio of the first extreme value to an extreme value of an electric field of the electromagnetic wave output toward the device under test, the second ratio being a ratio of the second extreme value to the extreme value of the electric field of the electromagnetic wave output toward the device under test.

14. A non-transitory computer-readable medium having a program of instructions for execution by a computer to perform an electromagnetic wave measurement process using an electromagnetic wave measurement device including an electromagnetic wave output device that outputs an electromagnetic wave having a frequency equal to or more than 0.01 THz and equal to or less than 100 THz toward a device under test including at least two layers; and an electromagnetic wave detector that detects reflected electromagnetic waves which are electromagnetic waves reflected by the respective at least two layers, the program causes the computer to perform:
measuring the device under test based on at least two extreme values of electric fields of the respective reflected electromagnetic waves and a time difference between times at which the electric fields of the respective reflected electromagnetic waves take the at least two extreme values, the at least two extreme values including a first extreme value and a second extreme value,
wherein the device under test is measured based on a product of a first ratio and a second ratio, or an absolute value of the product, the first ratio being a ratio of the first extreme value to an extreme value of an electric field of the electromagnetic wave output toward the device under test, the second ratio being a ratio of the second extreme value to the extreme value of the electric field of the electromagnetic wave output toward the device under test.

* * * * *